(12) United States Patent
Pereira et al.

(10) Patent No.: US 7,745,401 B2
(45) Date of Patent: Jun. 29, 2010

(54) ANTIFUNGAL PEPTIDES AND METHODS OF USE THEREOF

(75) Inventors: H. Anne Pereira, Edmond, OK (US); Paul Fidel, Mandeville, LA (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 460 days.

(21) Appl. No.: 11/497,178

(22) Filed: Jul. 31, 2006

(65) Prior Publication Data

US 2007/0135341 A1 Jun. 14, 2007

Related U.S. Application Data

(60) Provisional application No. 60/704,257, filed on Aug. 1, 2005.

(51) Int. Cl.
*A61K 38/00* (2006.01)
(52) U.S. Cl. .......................................... 514/12; 514/13
(58) Field of Classification Search ........................ None
See application file for complete search history.

(56) References Cited

U.S. PATENT DOCUMENTS

| 5,458,874 A | 10/1995 | Pereira et al. |
| 5,484,885 A | 1/1996 | Pereira et al. |
| 5,607,916 A | 3/1997 | Pereira et al. |
| 5,627,262 A | 5/1997 | Pereira |
| 5,650,392 A | 7/1997 | Pereira et al. |
| 5,877,151 A | 3/1999 | Pereira |
| 6,071,879 A | 6/2000 | Pereira |
| 6,107,460 A | 8/2000 | Pereira |
| 2003/0171281 A1* | 9/2003 | Krieger et al. ................ 514/12 |

OTHER PUBLICATIONS

Roberts et al. Chemistry for peptide and protein PEGylation. Advanced Drug Delivery Reviews 2002. vol. 54, pp. 459-476.*
J. Davies, J. Peptide Sci. 9:471-507(2003).
M. Hornef, et al. Nat. Immunol. 5(8):836-843(2004).
P. Li and P. Roller. Can. Top. In Med. Chem. 2:325-341(2002).
Technical Report TI-PEP05-0405 of Thermo Electron Corp. 2005.
PCT/US 06/30001, International Search Report, Mar. 27, 2007.
H. Anne Pereira, et al., Expression of CAP37, a Novel Inflammatory Mediator, in Alzheimer's Disease, Neurobiology of Aging, vol. 17, No. 5, pp. 753-759, 1996.
Denise McCabe, et al., Basic Residues in Azurodicin/HBP Contribute to Both Heparin Binding and Antimicrobial Activity, The Journal of Biological Chemistry, vol. 277, No. 30, Issue of Jul. 26, pp. 27477-27488, 2002.
David Campanelli, et al., Azurocidin and a Homologous Serine Protease from Neutrophils, J. Clin. Invest., vol. 85, Mar. 1990, pp. 904-915.

* cited by examiner

*Primary Examiner*—Anish Gupta
*Assistant Examiner*—Marcela M Cordero Garcia
(74) *Attorney, Agent, or Firm*—Dunlap Codding, P.C.

(57) ABSTRACT

A method of treating fungal infections by treatment with CAP37 peptides and derivatives thereof, including peptide analogs having serine or threonine substitutions at least one of the two cysteine residues therein. Other substitutions of the amino acid residues of the peptide are also contemplated.

20 Claims, 4 Drawing Sheets

ANTIFUNGAL PEPTIDES AND METHODS OF USE THEREOF

CROSS-REFERENCE TO RELATED APPLICATIONS

The present application claims the benefit under 35 U.S.C. §119(e) of U.S. Provisional Application Ser. No. 60/704,257, filed Aug. 1, 2005, the contents of which is expressly incorporated herein in its entirety.

STATEMENT REGARDING FEDERALLY SPONSORED RESEARCH OR DEVELOPMENT

Portions of this work were supported by Public Health Service grant AI28018 from the National Institutes of Health. The U.S. Government has certain rights to the invention described herein.

BACKGROUND

CAP37 (cationic antimicrobial protein of $M_r$ 37 kDa) was originally identified as a component of the oxygen-independent killing mechanism of the human neutrophil (PMN) and was demonstrated to have strong bactericidal activity for Gram negative organisms including *Salmonella typhimurium, Escherichia coli,* and *Pseudomonas aeruginosa* (Shafer et al., 1984; Shafer et al., 1986; Spitznagel 1990). Distinct from its effect on bacteria the native CAP37 protein has potent regulatory effects on host cells. It is an effective regulator of cells of the mononuclear phagocytic system such as monocytes (Pereira et al., 1990), microglia (Pereira et al., 2002) and macrophages (Larrick et al., 1991). It also regulates corneal epithelial (Ruan et al., 2002), endothelial (Lee et al., 2002; Lee et al., 2003) and smooth muscle cell functions (Gonzalez et al., 2004).

Structure function analysis of CAP37 enabled us to delineate its antibacterial domain to a region corresponding to residues 20 through 44 of the native molecule (Pereira et al., 1993). A peptide comprising this 25 amino acid sequence (CAP37(20-44)$_{nat}$) mimicked the antimicrobial activity of the native molecule (Pereira et al., 1993) and extended its range of activity to encompass *Staphylococcus aureus* and *Enterococcus faecalis*, two Gram positive organisms. The bactericidal activity of the peptide was pH dependent, with maximum activity obtained between pH 5.0 and 5.5. Replacement of the cysteine residues at positions 26 and 42 with serine residues (CAP37(20-44)$_{ser26/42}$) resulted in an inactive compound (Pereira et al., 1993). In vivo experiments demonstrated the efficacy of CAP37(20-44)$_{nat}$ in attenuating the lethal effects of *E. coli* lipopolysaccharide (LPS) in a conscious rat model of endotoxic shock (Bracket et al., 1997).

Infections due to the various *Candida* species can result in disease manifestations ranging from self limiting superficial infections to life threatening systemic infections (Nola et al., 2003). In the recent past there has been a dramatic increase in invasive fungal infections and *Candida* species are beginning to contribute substantially to serious hospital acquired infections (Clark and Hajjeh, 2002; Hobson 2003, Nola et al., 2003; Rapp 2004). The reasons for this are complex but can be attributed in major part to the latest advances in medicine leading to the increased survival of immunocompromised persons and the use of indwelling medical devices and catheters for treatment of hospitalized patients (Clark and Hajjeh 2002; Nola et al., 2003). The developing incidence of resistance to available anti-fungal drugs further compounds the clinical and public health problems associated with mycotic infections. New drugs having anti-fungal activity are needed. It is to this object that the present invention is directed.

DETAILED DESCRIPTION OF THE INVENTION

Figure 1:
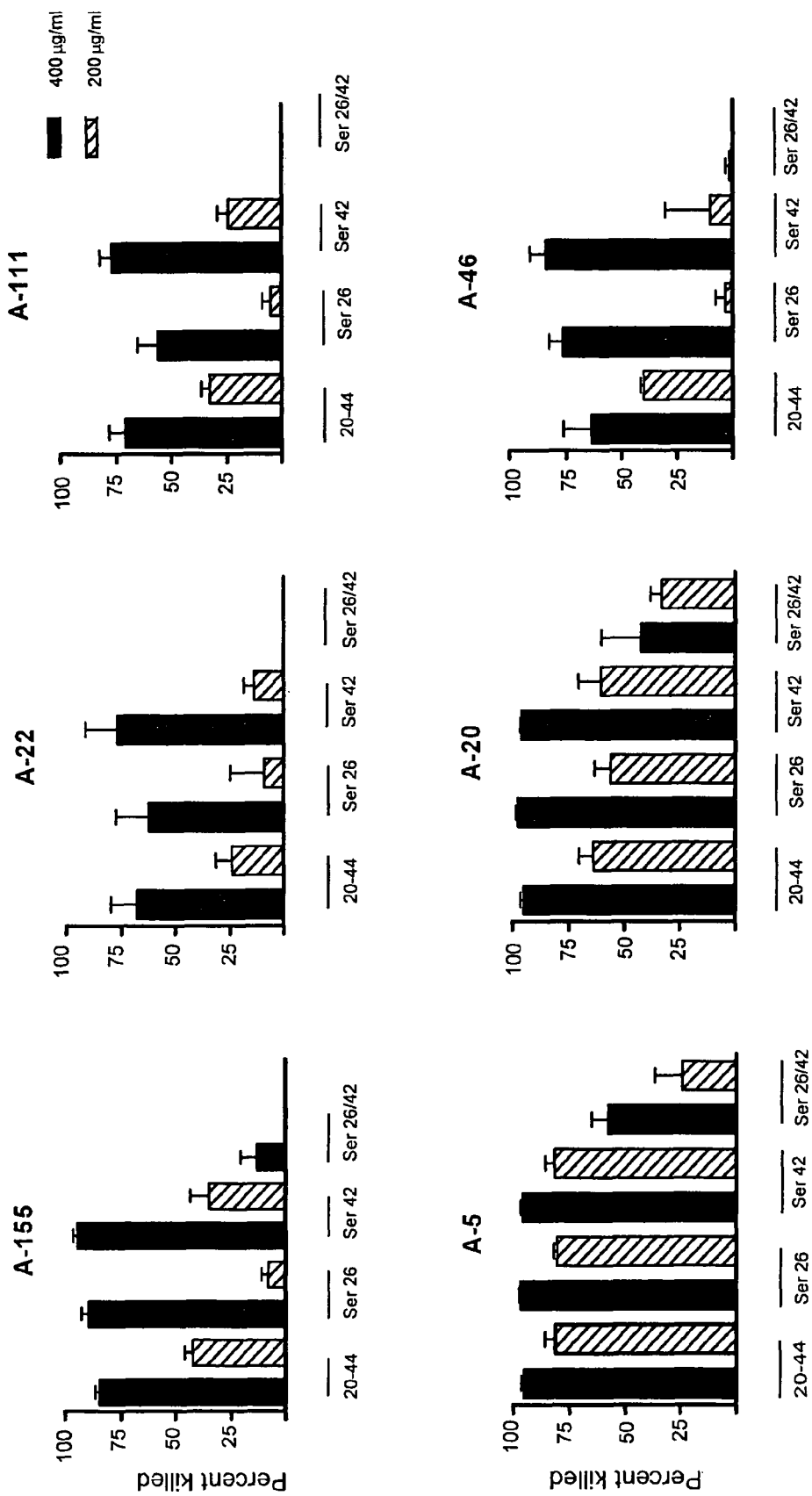
FIG. 1. is a graph showing the Candidacidal activity of the four CAP37 peptides. Activity of CAP37(20-44)$_{nat}$, CAP37(20-44)$_{ser26}$, CAP37(20-44)$_{ser42}$, and CAP37(20-44)$_{ser26/42}$, at 400 mg/ml (solid bar) and 200 mg/ml (diagonal stripes) was tested against clinical isolates of *Candida albicans* A-155, A-22 and A-111 (known to be fluconazole sensitive) and isolates A-5, A-20 and A-46 (known to be fluconazole resistant). The percent killed is determined as detailed in the materials and methods section. Values are expressed as ±standard error of the mean from three independent experiments performed in triplicate.

Demonstrated herein is the anti-fungal activity of peptides based on the native sequence of the antibiotic protein CAP37. The peptides can be used as anti-fungal agents, particularly against *Candida* sp.

CAP37 has traditionally been considered a PMN-derived protein since it is constitutively expressed in the granules of these cells. However, more recently we have demonstrated the presence of an inducible form of CAP37 (Lee et al., 2002; Pereira et al., 1997; Ruan et al., 2003; Gonzalez, et al., 2004; and Pereira et al., 2004). CAP37 can be expressed in endothelial cells lining the vasculature in inflammatory-mediated diseases such as Alzheimer's disease (Pereira et al., 1997) and atherosclerosis (Lee et al., 2002). In vitro studies indicate that induction is due to inflammatory mediators such as tumor necrosis factor—α (TNF-α), interleukin-1 (IL-1) and immunomodulatory substances such as LPS. In vivo studies employing a rabbit model of *S. aureus* keratitis, demonstrated the very early induction of CAP37 in the corneal epithelium, and in the endothelium lining vessels in the limbic circulation in response to infection (Ruan et al., 2002). Additionally we have demonstrated the expression of CAP37 in squamous epithelial cells of the skin, cells lining the hair follicles, acinar cells of the sebaceous glands and endothelial cells lining blood vessels in response to wounding using an in vivo rat model of wound repair (Pereira et al., 2004). Epithelial antibiotics have been demonstrated in the skin (Nizet et al., 2001; Sørensen et al., 2003; Shirafuji et al., 1999; Oren et al., 2003), mucosal surfaces lining the gastrointestinal tract (Frohm-Nilsson et al., 1999; Fellermann and Stange, 2001), oral surfaces (Dale 2000; Dale 2001), respiratory tract (Hiemstra 2001; Diamond et al., 2000; Huttner and Bevins, 1999) and genitourinary tract (Frohm-Nilsson et al., 1999; Malm et al., 2000). These antibiotic proteins are ideally located to serve as the first line of defense against invading pathogens. Whether expression of CAP37 occurs in mucosal linings of the host in response to *Candida* infections or whether the induction of CAP37 is compromised in mucosal and epithelial surfaces in patients with recurrent candidiasis suggesting a physiological role for CAP37 in the protection of the host against fungal infections is currently unknown. The study reported here describes for the first time that CAP37 peptides and analogs and derivatives based on the native sequence of CAP37 possess potent antifungal activity and suggest a more broad-spectrum anti-infective activity for the peptide than originally proposed.

In one series of experiments we used peptides based on the native CAP37 sequence including CAP37(20-44)$_{nat}$ and three peptide analogs (CAP37(20-44)$_{ser26}$, CAP37(20-44)$_{ser42}$, $_{CAP}$37(20-44)$_{ser26/42}$) in which the cysteine residues at positions 26 and/or 42 were replaced by serine residues as indicated in Table 1. We investigated the effect of substitutions at these two positions on the in vitro killing efficacy on a range of *Candida* species. Our findings demonstrate significant activity against *C. albicans* by the peptide based on the native sequence (CAP37(20-44)$_{nat}$) and the two analogs in which only a single cysteine residue were replaced (CAP37(20-44)$_{ser26}$ and CAP37(20-44)$_{ser42}$). The replacement of both cysteines significantly abrogated activity against *C. albicans* and many of the *Candida* species tested. While not wishing to be held to theory, these data suggested that intramolecular disulfide bonding was important but that the formation of a cyclic compound was not essential for anti-fungal activity since intermolecular interactions between two cysteine residues, which is possible with the two mono-cysteine substitutions, resulted in a peptide which retained killing activity.

TABLE I

CAP37 Peptides and Derivatives

| Peptide Name | Peptide Sequence | SEQ ID NO. |
|---|---|---|
| CAP37(20-44)$_{nat}$ | N-Q-G-R-H-F-C-G-G-A-L-I-H-A-R-F-V-M-T-A-A-S-C-F-Q | 1 |
| CAP37(20-44)$_{ser26}$ | N-Q-G-R-H-F-S-G-G-A-L-I-H-A-R-F-V-M-T-A-A-S-C-F-Q | 2 |
| CAP37(20-44)$_{ser42}$ | N-Q-G-R-H-F-C-G-G-A-L-I-H-A-R-F-V-M-T-A-A-S-S-F-Q | 3 |
| CAP37(20-44)$_{ser26/42}$ | N-Q-G-R-H-F-S-G-G-A-L-I-H-A-R-F-V-M-T-A-A-S-S-F-Q | 4 |
| CAP37(23-42)$_{nat}$ | R-H-F-C-G-G-A-L-I-H-A-R-F-V-M-T-A-A-S-C | 5 |
| CAP37(23-42)$_{ser26}$ | R-H-F-S-G-G-A-L-I-H-A-R-F-V-M-T-A-A-S-C | 6 |
| CAP37(23-42)$_{ser42}$ | R-H-F-C-G-G-A-L-I-H-A-R-F-V-M-T-A-A-S-S | 7 |
| CAP37(23-42)$_{ser26/42}$ | R-H-F-S-G-G-A-L-I-H-A-R-F-V-M-T-A-A-S-S | 8 |
| CAP37(20-44)$_{thr26}$ | N-Q-G-R-H-F-T-G-G-A-L-I-H-A-R-F-V-M-T-A-A-S-C-F-Q | 9 |
| CAP37(20-44)$_{thr42}$ | N-Q-G-R-H-F-C-G-G-A-L-I-H-A-R-F-V-M-T-A-A-S-T-F-Q | 10 |
| CAP37(20-44)$_{thr26/42}$ | N-Q-G-R-H-F-T-G-G-A-L-I-H-A-R-F-V-M-T-A-A-S-T-F-Q | 11 |
| CAP37(23-42)$_{thr26}$ | R-H-F-T-G-G-A-L-I-H-A-R-F-V-M-T-A-A-S-C | 12 |
| CAP37(23-42)$_{thr42}$ | R-H-F-C-G-G-A-L-I-H-A-R-F-V-M-T-A-A-S-T | 13 |
| CAP37(23-42)$_{thr26/42}$ | R-H-F-T-G-G-A-L-I-H-A-R-F-V-M-T-A-A-S-T | 14 |

Figure 2:
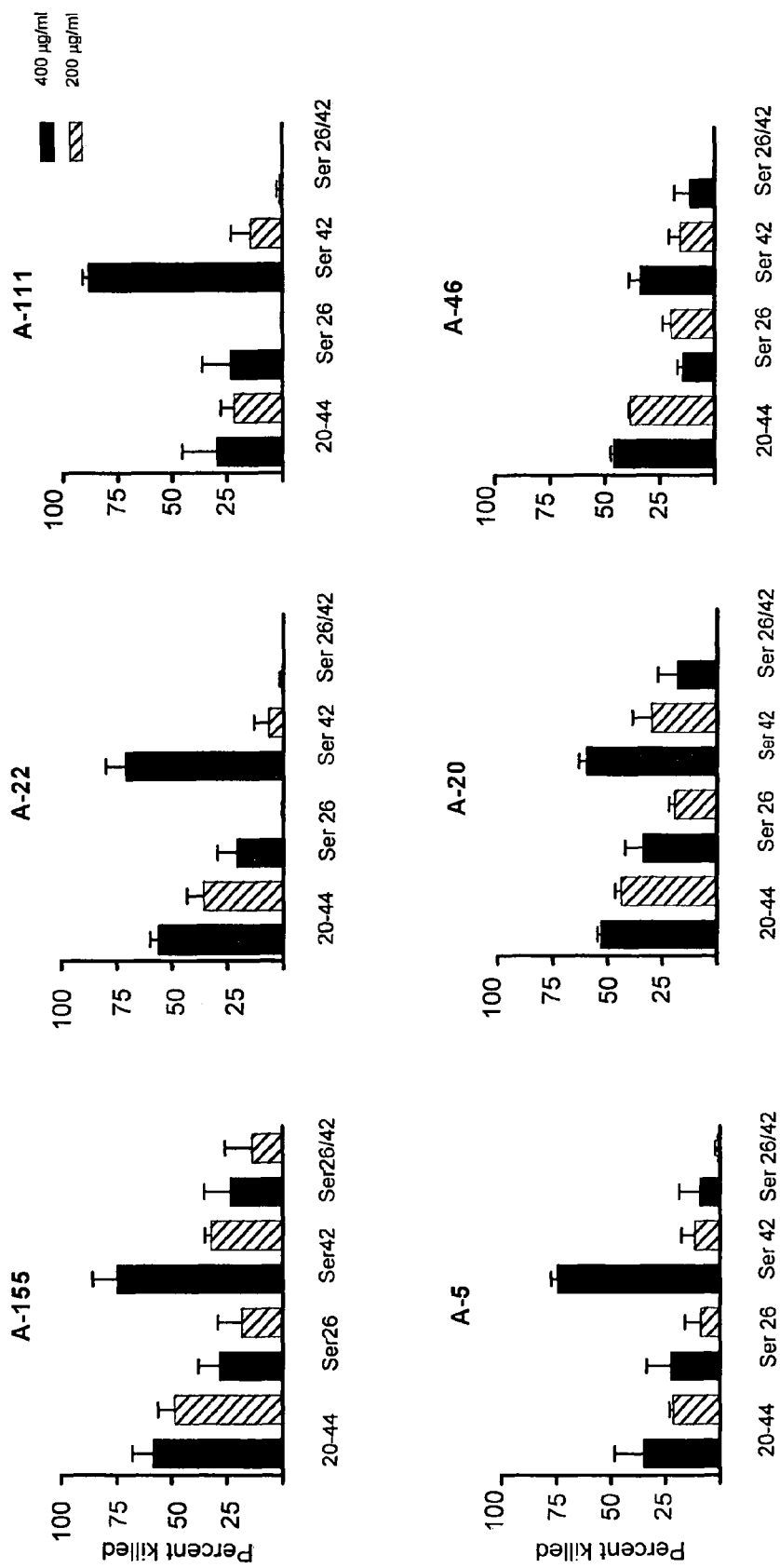
FIG. 2. is a graph showing the activity of CAP37 peptides on hyphal form of *C. albicans*. Activity of CAP37(20-44)$_{nat}$, CAP37(20-44)$_{ser26}$, CAP37(20-44)$_{ser42}$, and CAP37(20-44)$_{ser26/42}$, at 400 mg/ml (solid bar) and 200 mg/ml (diagonal stripes) was tested against hyphal forms of the clinical isolates of *Candida albicans* A-155, A-22 and A-111, A-5, A-20 and A-46. The percent killed was determined as detailed in the materials and methods section. Values are expressed as ±standard error of the mean from three independent experiments performed in triplicate.

The activity of the CAP37(20-44)$_{nat}$, CAP37(20-44)$_{ser26}$ and CAP37(20-44)$_{ser42}$ peptides against the fluconazole resistant mucosal isolates (A-5, A-20, A-46) was striking, with strong killing (<5% survival) obtained against two of the isolates (A-5 and A-20) and >75% killing obtained against isolate A-46 (FIG. 2). These findings are particularly pertinent to the recent emergence of fluconazole resistant isolates of *Candida albicans* and non-albicans species that will require treatment with new therapeutics with novel or alternative mechanisms of action (Jabra-Rizk et al., 2004; Sullivan et al., 2004). In addition to the important finding that CAP37 peptides had activity against fluconazole resistant mucosal isolates of *C. albicans*, FIG. 3 indicates that the peptides showed potent activity against *C. guilliermondii*, and *C. parapsilosis* at 37.5 μM concentration. *C. parapsilosis* is most often isolated from critically ill patients in intensive care units who typically have indwelling catheters and devices while undergoing treatment (Kuhn et al., 2004). Almost 100% of the starting inocula of *C. pseudotropicalis* and *C. tropicalis* were killed with peptide concentrations of 150 µM. *C. tropicalis* is being increasingly isolated from blood cultures of patients with leukemias, other neoplasias and those in intensive care units (Warn et al., 2002). Of the peptides, CAP37(20-44)$_{ser42}$ was more effective against *C. dubliniensis* than CAP37(20-44)$_{nat}$. *C. dubliniensis* is a newly identified species that is seldom found in healthy persons but tends to be found as the causative agent of oropharyngeal infections mainly in HIV-infected individuals (Sullivan et al, 2004). The peptides were not active against *C. glabrata, C. krusei* and *S. cerevisiae* and had modest activity against the hyphal forms of *C. albicans*.

The concentrations of peptide required to achieve fungicidal activity are approximately twice that demonstrated to kill the Gram negative isolates *S. typhimurium, E. coli* and *P. aeruginosa* (Pereira et al., 1993). This range in activity is not uncommon amongst cationic antimicrobial peptides which tend to have specificity and potency towards certain bacterial species, fungi, parasites and or viruses. Besides CAP37, the PMN contains several cationic antimicrobial peptides including the defensins, hCAP18/LL37, bactericidal permeability increasing protein (BPI), and lactoferrin (Spitznagel, 1990: Ganz and Weiss, 1997). The defensins are particularly active against *C. albicans* (Selsted et al., 1985; Hoover et al., 2003). Synthetic peptides based on the first cationic domain of the amino-terminus of human lactoferrin were shown to have candidacidal activities at micromolar levels (Lupetti et al., 2000). Antimicrobial peptides from human platelets have also been shown to have antimicrobial activities (Tang et al., 2002). Of the seven peptides isolated from platelets, only "Regulated upon Activation Normal T cell Expressed and Secreted" protein (RANTES) and platelet factor-4 (PF-4) exhibited candidacidal activity Their activity like the CAP37 peptides was pH dependent, being maximally active at pH 5.5 (Tang et al., 2002). Active peptide concentrations used ranged between 150 µg and 1.0 mg/ml depending on the molecular weight of each peptide (Tang et al., 2002). Another well known candidacidal molecule is salivary histatin-5 (Tsai and Bobek 1997; Edgerton et al., 2000). Salivary histatin-5 concentrations of 15 µM have been demonstrated to kill between 80 and 100% of *C. albicans* blastospores (Tsai and Bobek, 1996). Synthetic histatin analogs based on the C-terminal fungicidal domain of histatin-5 have been shown to be effective against *C. albicans* (Helmerhorst et al., 1997), *C. krusei*, fluconazole resistant strains of *C. glabrata* and *Aspergillus fumigatus* (Helmerhorst et al., 1999).

The use of natural cationic peptides as novel therapeutics in the treatment of infections is gaining enthusiasm in the scientific and biotechnology communities. The major drawback to conventional antibiotics is the rapidity with which microorganisms can gain multiple resistance patterns. The exact mechanism as to how these cationic antimicrobial peptides including those described herein, kill microorganisms is not entirely known. However, without wishing to be constrained by theory, it is believed that the principal bactericidal mechanism is the permeabilization of the microorganism membrane through porin channels and self promoted uptake pathways (Hancock, 1997). Cationic antimicrobial peptides do not appear to be involved in the metabolic pathways of the organisms and thus may not be involved in common resistance mechanisms. Hancock (1997) has shown that cationic peptides do not induce resistant mutants even after as many as 20 passages on antibiotic concentrations close to minimum inhibitory concentration. Clearly, although the mode of action of the CAP37 peptides is yet to be determined, without wishing to be held to theory, it appears to be different from the mechanism of action of azole-based drugs, since it kills fluconazole resistant and sensitive strains equally well.

Materials and Methods

Peptide Synthesis.

Peptides were synthesized by solid-phase synthesis on a peptide synthesizer as previously described (Pereira et al., PNAS 1993). Purity of the peptides was ascertained. The mass of the peptide was confirmed by mass spectrometry. Peptides were synthesized predicated on previous findings that a synthetic peptide (CAP37(20-44)$_{nat}$) based on the native amino acid sequence of CAP37 consisting of residues 20 through 44 had potent bactericidal activity for a number of Gram negative organisms (Pereira et al., PNAS 1993). An inactive analog of this peptide in which the cysteine residues at positions 26 and 42 were replaced by serine residues (CAP37(20-44)$_{ser26/42}$) (Pereira et al., PNAS 1993) was used as an inactive control peptide. In addition, two other peptide analogs were synthesized. One peptide had the cysteine residue at position 26 replaced by a serine (CAP37(20-44)$_{ser26}$) and the other had the cysteine residue at position 42 replaced by a serine (CAP37(20-44)$_{ser42}$).

Fungal Isolates and Culture Conditions.

Isolates used in this study included *Candida albicans* (ATCC 28367), three fluconazole sensitive mucosal isolates of *C. albicans*, designated A-22, A-111 and A-155, three fluconazole resistant mucosal isolates of *C. albicans* designated A-46, A-5, and A-20, and a blood isolate of *C. albicans* designated WDO. Isolates were stored frozen at −70° C. and streaked onto Sabouraud Dextrose Agar (Sigma, St. Louis, Mo.) plates and maintained on plates at 4° C., with subculturing onto new plates approximately every 10 days for the duration of the studies. Fluconazole resistance was evaluated. Three clinical isolates of *C. glabrata*, two clinical isolates of *C. dubliniensis*, and single isolate each of *C. krusei, C. guillermondii, C. parapsilosis, C. pseudotropicalis* and *C. tropicalis* and two isolates of *Saccharomyces cerevisiae* were also used in this study and were maintained on Sabouraud Dextrose agar plates at 4° C. A single yeast colony was cultured overnight at 33° C. in 1% phytone peptone broth (Becton Dickinson, Sparks Md.) with 0.1% D-glucose (Sigma).

Induction of Hyphae.

To induce hyphal formation a single colony of *C. albicans* isolates A-5, A-20, A-22, A-46, A-11 and A-155 from a Sabouraud Dextrose agar plate was transferred to 1% phytone peptone broth with 0.1 glucose and grown overnight at 33° C. An aliquot (500 µl) of the overnight culture was subcultured in 5 ml of RPMI-1640 (Celigro Mediatech Inc, Herndon, Va.)) with 10% fetal calf serum (Invitrogen, Grand Island, N.Y.) for 90 min at 37° C. Hyphal formation was determined under phase microscopy.

In Vitro Candidacidal Assay.

Stock solutions of all peptides were made up at concentrations of 1 mg/ml in sterile endotoxin-free water for irrigation (Baxter, Deerfield, Ill.). Subsequent dilutions were all made in tryptone saline pH 5.5 (Shafer et al., Infect Immun, 1984). An aliquot (100 µl) of an overnight culture of a single colony grown at 33° C. in 1% phytone peptone broth with 0.1% glucose was subcultured in 5 ml of 1% phytone peptone broth with 0.1% glucose and incubated in a shaking water bath (80 oscillations per min, Precision, Winchester, Va.) for 90 min at 33° C. to yield a logarithmic culture. Cell cultures under these conditions were found to consist predominantly of blastospores as determined by phase contrast microscopy. The optical density was read and the culture adjusted to 500 blastospores/100 µl in tryptone saline pH 5.5 (Shafer et al., Infect Immun, 1984). To 100 µl of the organism suspension in a 96 well sterile polystyrene microtiter plate (Becton Dickinson, Franklin Lakes, N.J.) was added 100 μl of the peptide (final concentrations 400 μg/ml and 200 μg/ml) or 100 μl of tryptone saline. The latter served as a control. The microtiter plate was incubated at 37° C. for 4 hr and 100 μl of the contents from each well was plated on Sabouraud Dextrose agar plates and incubated at 37° C. overnight. The colony forming units (cfu) were counted and the fungicidal activity was expressed as percent killed and calculated according to the following equation: [(control cfu−test cfu)/control cfu]×100=% killed. Control cfu is indicated by the number of colonies present after 60 min of incubation in tryptone saline alone in the absence of peptide. Test cfu is determined by counting the number of colonies present after incubation in tryptone saline containing the peptide. Each experimental point was performed in triplicate.

Methods for Fungicidal Assay

Yeast viability was also assessed using the FUN-1 Live/Dead Yeast Viability Kit (Molecular Probes, Eugene, Oreg.). The methodology employed was essentially according to the protocol provided by the vendor for use with fluorescent microscopy. Briefly, yeast cultures were prepared exactly as stated above. $C.$ $glabrata,$ $C.$ $pseudotropicalis,$ $C.$ $albicans$ (fluconazole sensitive isolate) and $S.$ $cerevisiae$ ($5 \times 10^5$ cfu in 100 μl of tryptone saline) were incubated (37° C. for 2 hr) in the absence or presence of peptide (CAP37(20-44)$_{nat}$ and CAP37(20-44)$_{ser26/42}$) at a final concentration of 400 μg/ml. At the end of the incubation period, the samples were transferred to microcentrifuge tubes and centrifuged (10,000×g for 3 min at room temperature). The supernatant was removed and the pellet resuspended in 25 μl of GH solution (2% D-glucose containing 10 mM Na-HEPES, pH 7.2) as described in the technical data sheet provided by the vendor. A working solution of the FUN-1 reagent (100 μl of 10 μM) was prepared from 10 mM stock solution and 25 μl (final concentration 5 μM) added to the yeast and incubated at room temperature for 30 min. A sample (10 μl) was placed on a microscope slide and staining observed under a Leica TCS NT confocal microscope using Ar-488 and Kr-568 Lasers and 63x Plan APO 1.2 NA water immersion objective. Images were scanned and analyzed using the Leica TCS software.

Statistical Analysis.

Data are presented as mean±standard error from three or four independent experiments performed in triplicate.

Results

Synthesis of Peptides.

Peptides synthesized for these studies are represented in Table 1. CAP37(20-44)$_{nat}$ contains two cysteine residues corresponding to the positions 26 and 42 native CAP37 protein which form a disulfide bridge in the native CAP37 molecule (Pohl et al., FEBS Lett 1990). Therefore, the importance of these two cysteine residues was assessed for activity of the peptide by replacing both cysteines with serine residues (CAP37(20-44)$_{ser26/42}$) or a single cysteine with a serine at position 26 (CAP37(20-44)$_{ser26}$) or 42 (CAP37(20-44)$_{ser42}$). The replacement of either one or both cysteine residues confers on the peptide the inability to form a disulfide bond and therefore interferes with the possible formation of a cyclic structure. Without wishing to be held to theory, the replacement of one cysteine at either position interferes with the formation of a cyclic structure but still enables dimerization.

Standardization of In Vitro Candidacidal Assay.

$C.$ $albicans$ (ATCC 28367) was used to standardize the in vitro killing assay. We explored the optimal growth conditions (temperature and time, 25° C. for 5 h and 33° C. for 90 min), numbers of blastospores per well (200, 400, 500, 600, 800, and 1000 cfu), range of peptide concentrations (750, 500, 400, 200 and 100 μg/ml) and the contact time between peptide and $Candida$ (1, 2 and 4 hr) for killing to occur. Data indicated that there was no significant difference between using $Candida$ that had been grown for 5 h at 25° C. or for 90 min at 33° C. The 90 minute incubation was more convenient technically and was therefore employed routinely. The optimum numbers of cfu per well was determined to be 500 and an incubation time of 4 hr at 37° C. between $Candida$ and peptide was required to obtain optimal killing. Dose dependent killing was obtained with the varying concentrations of CAP37(20-44)$_{nat}$. However, the best distinction between active and inactive peptide was obtained at 400 μg/ml or 150 μM.

Fungicidal activity of CAP37 peptides on fluconazole sensitive and resistant strains of $C.$ $albicans.$ Peptides CAP37(20-44)$_{nat}$, CAP37(20-44)$_{ser26}$, and CAP37(20-44)$_{ser42}$ were strongly active against the fluconazole sensitive clinical isolates A-155, A-22 and A-111 at 400 μg/ml, with a range of activity between 60% and 94% killed depending on the isolate (FIG. 1). Isolate A-155 appeared to be the most sensitive with 80-94% of organisms killed. There was no statistical difference between the activities of the three peptides for any given isolate. In marked contrast to the activity of these three peptides was the lack of activity of CAP37(20-44)$_{ser26/42}$ in which both cysteine residues were substituted by serine residues.

Peptides CAP37(20-44)$_{nat}$, CAP37(20-44)$_{ser26}$, and CAP37(20-44)$_{ser42}$ were highly active against fluconazole resistant isolates A-5 and A-20 with significant activity obtained even at the lower concentration (200 μg/ml or 75 μM) of peptide. Higher concentrations (400 μg/ml) of the peptides were required for activity against the fluconazole resistant isolate A-46. Whereas CAP37(20-44)$_{ser26/42}$ peptide considered as inactive was moderately active against isolates A-5 and A-20.

The effect of peptides CAP37(20-44)$_{nat}$, CAP37(20-44)$_{ser26}$, and CAP37(20-44)$_{ser42}$ on the fluconazole resistant species A-5, A-20, and A-46 and the fluconazole sensitive strain A-155 was fungicidal rather than fungistatic since the viable colony counts in the presence of the peptides were less than the starting inoculum.

Fungicidal Activity of CAP37 Peptides on Hyphal Forms of $C.$ $albicans.$

The CAP37 peptides were less active on the hyphal forms of the clinical isolates of $C.$ $albicans$ when compared to their activities on the blastospores (FIG. 2). When comparing activity between peptides CAP37(20-44)$_{nat}$, CAP37(20-44)$_{ser26}$, and CAP37(20-44)$_{ser42}$, it would appear that greater activity was obtained with CAP37(20-44)$_{ser42}$ against hyphal forms than with the other CAP37 peptides.

Fungicidal Activity of CAP37 Peptides on Various $Candida$ Species.

Figure 3:
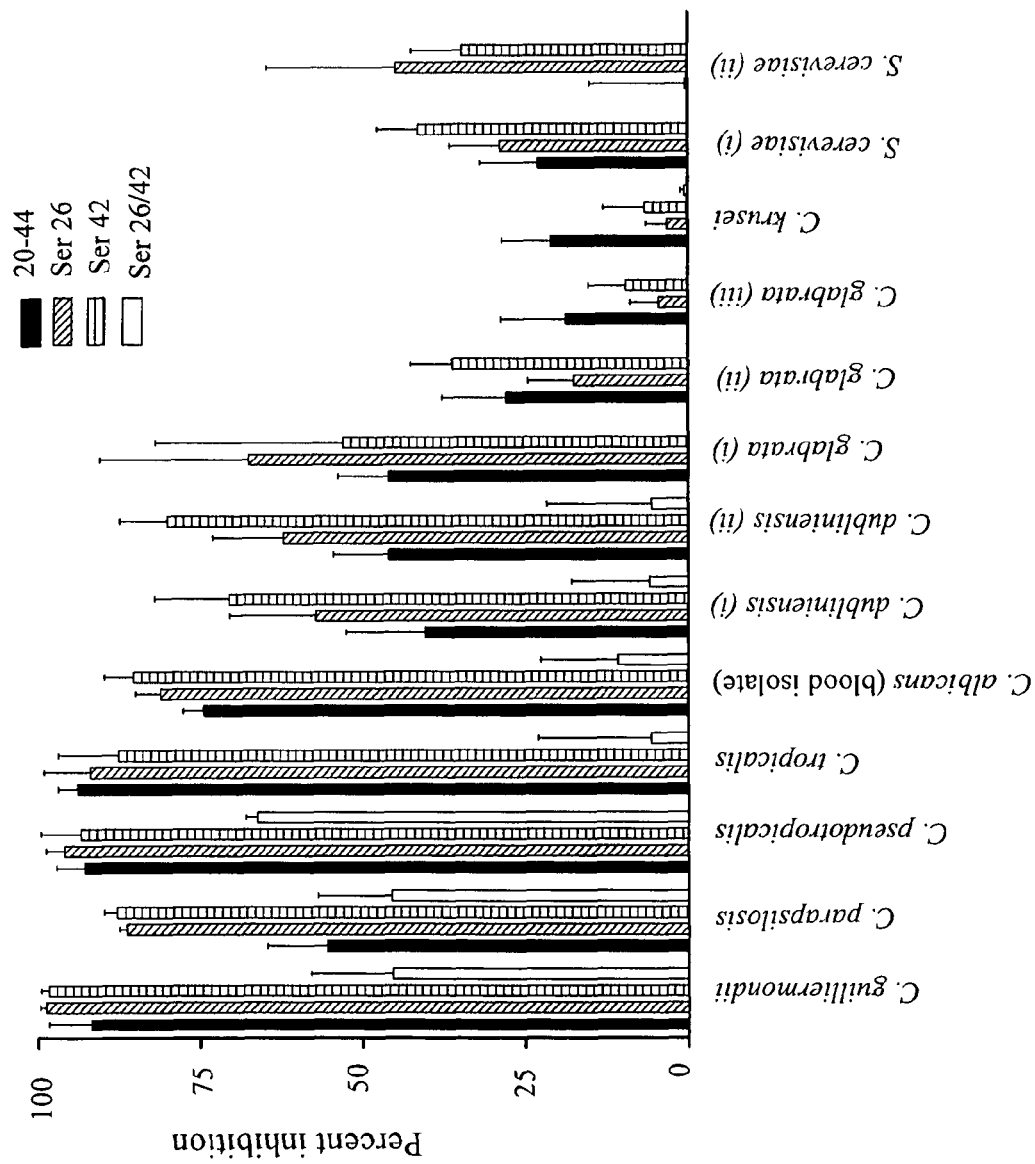
FIG. 3. is a graph showing the activity of CAP37 peptides against various *Candida* species. The fungicidal activity of CAP37(20-44)$_{nat}$, CAP37(20-44)$_{ser26}$, CAP37(20-44)$_{ser42}$, and CAP37(20-44)$_{ser26/42}$ was tested on *C. guilliermondii, C. parapsilosis, C. pseudotropicalis, C. tropicalis,* a blood isolate of *C. albicans*, two isolates of *C. dubliniensis*, three isolates of *C. glabrata*, one isolate of *C. krusei* and two isolates of *S. cerevisiae*. The peptide concentrations for *C. guilliermondii* and *C. parapsilosis* were 100 μg/ml (37.5 μM) whereas all other strains were assayed with the peptide concentrations at 400 μg/ml (150 μM). Values are expressed as ±standard error of the mean from three to four independent experiments performed in triplicate.

The effect of CAP37 peptides varied depending on the different species of $Candida$ tested (FIG. 3). CAP37 peptides were most effective on $C.$ $guilliermondii$ and $C.$ $parapsilosis$. Peptide concentrations as low as 100 μg/ml (37.5 μM) were fungicidal for these two species. $C.$ $pseudotropicalis$ was also extremely sensitive to all the CAP37 peptides. As with $C.$ $guilliermondii$ and $C.$ $parapsilosis$ some activity was also obtained with peptide CAP37(20-44)$_{ser26/42}$ although significantly less than with the other three CAP37 peptides. $C.$ $tropicalis$ and a blood isolate of $Candida$ were also killed by CAP37(20-44)$_{nat}$, CAP37(20-44)$_{ser26}$, and CAP37 (20-44)$_{ser42}$. The activity on all of the above species was fungicidal rather than fungistatic. The CAP37 peptides (CAP37(20-44)$_{nat}$, CAP37(20-44)$_{ser26}$, and CAP37(20-44)$_{ser42}$) were effective against both isolates of $C.$ $dubliniensis$ and one isolate of $C.$ $glabrata$, although to a lesser extent. CAP37 peptides were ineffective against two of the *C. glabrata* isolates, *C. krusei* and the two isolates of *S. cerevisiae*.

Figure 4:
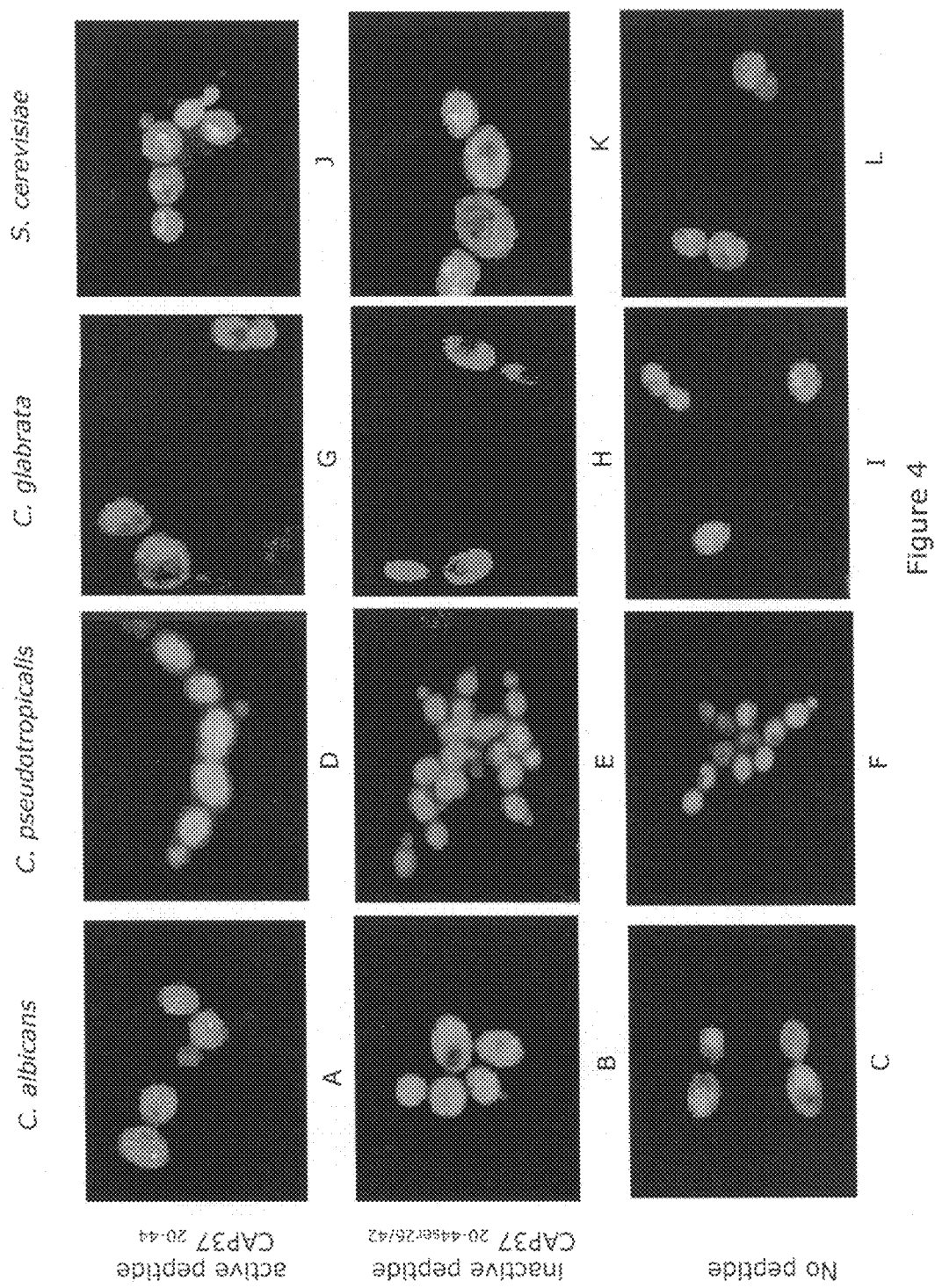
FIG. 4. shows fungicidal activity of CAP37 determined with the FUN-1 vital dye and confocal microscopy. We selected a fluconazole sensitive *C. albicans* isolate (images A-C), *C. pseudotropicalis* (images D-F), a *C. glabrata* isolate (images G-I) and a *S. cerevisiae* isolate (images J-L) to perform these studies. The fungal isolates were incubated with CAP37(20-44)$_{nat}$ peptide, CAP37(20-44)$_{ser26/42}$ peptide and in the absence of peptide. Cells that stain red are alive and those that stain uniformly green or green-yellow are dead. Representative digital images from three independent experiments are shown.

Antifungal activity of CAP37 peptides is fungicidal. We used confocal microscopy and the fluorescent dye FUN-1 to assess cell viability. We selected a fluconazole sensitive *C. albicans* isolate and *C. pseudotropicalis* that were sensitive to CAP37$_{20-44}$, and one of the *C. glabrata* and *S. cerevisiae* isolates as examples of fungi that were not affected by the peptides as determined by the CFU assay. Using this technique we observed good correlation between the previous data using colony counts and the microscopic evaluation. Representative views of the confocal data (FIG. 4) show that approximately 70-80% of all *C. albicans* blastoconidia stained green or green-yellow indicating that the majority of yeast cells were dead when incubated with CAP37(20-44)$_{nat}$ peptide. On the other hand the relatively inactive peptide (CAP37(20-44)$_{ser26/42}$) showed only 30% of the blastoconidia to be alive. Treatment of *C. pseudotropicalis* with peptide CAP37(20-44)$_{nat}$ showed killing of >95% of the cells. Similar results were obtained with the inactive peptide (CAP37(20-44)$_{ser26/42}$), confirming the results we obtained with the colony forming unit assay. Studies performed with *C. glabrata* and *S. cerevisiae* mirrored data obtained with the colony forming unit assay; approximately 10-15% of cells were killed by the active peptide and virtually all cells were viable in the presence of the inactive peptide. A control in which the yeast cells were incubated in the absence of peptide had no effect on viability.

Utility

Peptides which can be used as anti-fungal therapeutics in accordance with the present invention include peptides described herein as well as peptides described in U.S. Pat. Nos. 6,107,460; 6,514,701; and 6,730,659; the specification of each of which is hereby expressly incorporated by reference herein in its entirety.

As noted elsewhere herein, the invention contemplates in preferred embodiments the use of CAP37(20-44)$_{nat}$ (linear, or cyclized between the cysteines), CAP37(20-44)$_{ser26}$, CAP37(20-44)$_{ser42}$, and CAP37(20-44)$_{ser26/42}$ as antifungal treatments. The invention further comprises the use of peptides similar to peptides CAP37(20-44)$_{nat}$, CAP37(20-44)$_{ser26}$, CAP37(20-44)$_{ser42}$, and CAP37(20-44)$_{ser26/42}$ except wherein the N-terminal three amino acids and C-terminal two amino acids are truncated (CAP37(23-42)$_{nat}$ (linear, or cyclized between the cysteines), CAP37(23-42)$_{ser26}$, CAP37(23-42)$_{ser42}$, and CAP37(23-42)$_{ser26/42}$). Alternatively, each of these serine-substituted peptides can be alternatively substituted with threonine, (i.e., SEQ ID NO. 9-14). Further, the CAP37 peptide or peptide derivative used herein may comprise at least one of the following substitutions: phenylalanine replaced by tyrosine; glycines replaced by alanines; valine replaced by alanine, leucine, or isoleucine; alanine replaced by leucine, isoleucine or valine; leucine replaced by alanine, isoleucine or valine; isoleucine replaced by valine, leucine or alanine; serine replaced by histidine, arginine, or lysine; and threonine replaced by serine.

As noted elsewhere herein, the peptide derivative may be a derivative of CAP37(20-44) peptide or CAP37(23-42) modified as described above. In one alternative embodiment the peptide used may comprise CAP37(120-146), i.e. SEQ ID NO: 16. Alternatively the entire CAP37 protein may be used in the antifungal treatment of the present invention.

The present invention contemplates a method of treating a fungal infection in a patient, subject or mammal, or prophylactically preventing a fungal infection in a patient, subject or mammal comprising administering to the patient, subject or mammal a therapeutically effective amount of a peptide described herein.

Further, the peptide contemplated herein for use as an antifungal treatment may comprise a peptide having 20, 21, 22, 23, 24, or 25 residues and comprising the sequence (SEQ ID NO: 15):

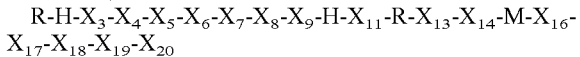

wherein $X_3$ and $X_{13}$ are phenylalanine, tyrosine, arginine, lysine or histidine; $X_4$ is selected from cysteine, serine, threonine, arginine, lysine or histidine; $X_5$ and $X_6$ are selected from glycine, alanine, arginine, lysine or histidine; $X_7$, $X_{11}$, and $X_{14}$ are selected from alanine, leucine, isoleucine, valine, arginine, lysine or histidine. $X_9$, $X_{17}$, and $X_{18}$ are selected from alanine, leucine, isoleucine and valine; $X_{16}$ is serine or threonine; $X_{19}$ is selected from serine, threonine, histidine, arginine and lysine; $X_{20}$ is selected from cysteine, serine and threonine; R is arginine; H is histidine; and M is methionine, and wherein the peptide may comprise one, two, or three additional residues on the N-terminal end and one or two additional residues on the C-terminal end of the peptide and wherein in one embodiment for example $X_3$-$X_7$ could be arginine and $X_{11}$-$X_{14}$ could be lysine.

Any of the peptides described herein may be used alone or in combination as antifungal treatments. In example any of SEQ ID NO: 1-16 may be used alone or in combination as a "cocktail" of peptides, further, where the peptides are conjugated to a polymer such as a PEG, various of the peptides of SEQ ID NO: 1-16 may be attached to the same PEG molecule. Further, any of the peptides of the present invention may be dimerized, for example, to form homodimers or heterodimers, such as a CAP37(20-44)$_{nat}$ dimer, a CAP37(20-44)$_{ser26}$ dimer, a CAP37(20-44)$_{ser42}$ dimer, or a CAP37(20-44)$_{ser26}$-CAP37(20-44)$_{ser42}$ dimer, for example. For the intramolecular cyclization, a disulfide bridge between the two cysteines is formed. Dimerization of peptides and intramolecular cyclization between thiol groups is well known in the art and a detailed explanation thereof is not deemed necessary herein. However, an example of these processes are shown in Technical Report TI-PEP05-0405 of Thermo Electron Corp. 2005, included herein by reference in its entirety. Dimers could be linked via "intermolecular oxidation", for example, the thiol group attached to the cys at position 26 would be linked to a SH group from another peptide having a cys 26 giving a homodimer. Similarly one could cyclize the SH group at cys 42 with an SH group on a cys 42 from another peptide, giving a cys 42 homodimer. In a third alternative, the thiol groups between cys 42 and cys 26 could be linked to give a heterodimer. Other references which show the state of the art of cyclizations and dimerization include J. Davies, J. Peptide Sci. 9:471-501(2003); P. Li and P. Roller. Can. Top. In Med. Chem. 2:325-341 (2002); and M. Hornef, et al. Nat. Immunol. 5(8):836-843(2004) all of which are expressly incorporated by reference herein in their entirety.

The present invention further comprises a DNA molecule having a nucleotide sequence encoding a peptide having an amino acid sequence as defined in any of the amino acid sequences listed or described herein, in particular, those having substituted cysteine residues at positions 26 or 42.

The present invention contemplates using the peptides described herein and/or effective subunits thereof both to treat ongoing fungal infections and to prophylactically treat an individual who may have a risk of such infection.

The peptide used in the present invention, synthetically or recombinantly produced, may be used as a pharmaceutical composition when combined with a pharmaceutically acceptable carrier. Such a composition may contain, in addition to the peptide and carrier, diluents, fillers, salts, buffers, stabilizers, solubilizers, and other materials well known in the art. Suitable carriers, vehicles and other components of the formulation are described, for example, in *Remingtons' Pharmaceutical Sciences*, (Mack Publishing Co., 1980 or latest edition). The term "pharmaceutically acceptable" means a non-toxic material that does not interfere with the effectiveness of the biological activity of the active ingredient(s). The characteristics of the carrier will depend on the route of administration.

The pharmaceutical composition of the invention may be in the form of a liposome in which isolated peptide is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are expressly incorporated herein by reference in their entireties.

A therapeutically effective amount of a compound of the present invention refers to an amount which is effective in controlling, reducing, or inhibiting a fungal infection. The term "controlling" is intended to refer to all processes wherein there may be a slowing, interrupting, arresting, or stopping of the progression of the infection and does not necessarily indicate a total elimination of the infection symptoms.

The term "therapeutically effective amount" is further meant to define an amount resulting in the improvement of any parameters or clinical symptoms characteristic of a fungal infection. The actual dose will vary with the patient's overall condition, the seriousness of the symptoms, and counter indications.

As used herein, the term "subject" or "patient" refers to a warm blooded animal, inparticular a mammal, which is afflicted with a fungal infection. It is understood that guinea pigs, dogs, cats, rats, mice, horses, goats, cattle, sheep, zoo animals, livestock, primates, and humans are examples of animals within the scope of the meaning of the term.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific fungal disease or condition involved; the degree of or involvement or the severity of the fungal disease or condition; the response of the individual subject; the particular compound administered; the mode of administration; the bioavailability characteristic of the preparation administered; the dose regimen selected; the use of concomitant medication; and other relevant circumstances.

A therapeutically effective amount of a compound of the present invention also refers to an amount of the compound which is effective in controlling or reducing the fungal infection.

A therapeutically effective amount of the compositions of the present invention will generally contain sufficient active ingredient (i.e., the peptide) to deliver from about 0.1 µg/kg to about 100 mg/kg (weight of active ingredient/body weight of patient). Preferably, the composition will deliver at least 0.5 µg/kg to 50 mg/kg, and more preferably at least 1 µg/kg to 10 mg/kg.

Practice of the method of the present invention comprises administering to a subject a therapeutically effective amount of the peptide in any suitable systemic or local formulation, in an amount effective to deliver the dosages listed above. An effective, particularly preferred dosage of the peptide for substantially inhibiting the fungal infection is 1 µg/kg to 1 mg/kg of the peptide. The dosage can be administered on a one-time basis, or (for example) from one to five times per day or once or twice per week, or continuously via a venous drip, depending on the desired therapeutic effect.

As used herein, the term "therapeutically effective amount" means the total amount of each active component of the pharmaceutical composition or method that is sufficient to show a meaningful patient benefit, i.e., reduction of fungal infection. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of the peptide composition is administered to a mammal having a fungal disease state. Peptide may be administered in accordance with the method of the invention either alone or in combination with other therapies.

Administration of peptide used in the pharmaceutical composition or to practice the method of the present invention can be carried out in a variety of conventional ways, including orally, by inhalation (e.g., for sinus fungal infections), rectally, or by cutaneous, subcutaneous, intraperitoneal, vaginal, or intravenous injection. Oral formulations my be formulated such that the peptide passes through a portion of the digestive system before being released, for example it may not be released until reaching the small intestine, or the colon.

When a therapeutically effective amount of peptide is administered orally, the peptide will be in the form of a tablet, capsule, powder, solution or elixir. When administered in tablet form, the pharmaceutical composition of the invention may additionally contain a solid carrier such as a gelatin or an adjuvant. The tablet, capsule, and powder preferably contains from about 5 to 95% peptide. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, 35 propylene glycol or polyethylene glycol. When administered in liquid form, the pharmaceutical composition preferably contains from about 0.005 to 95% by weight of peptide. For example, 100-1000 mg of active ingredient once to twice a day could be administered orally.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of this invention can be tabletted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, and buffers as are known in the art.

When a therapeutically effective amount of peptide is administered by intravenous, cutaneous or subcutaneous injection, peptide is preferably in the form of a pyrogen-free, parenterally acceptable aqueous solution or suspension. The preparation of such parenterally acceptable peptide solutions, having due regard to pH, isotonicity, stability, and the like, is within the skill in the art. A preferred pharmaceutical composition for intravenous, cutaneous, or subcutaneous injection should contain, in addition to peptide an isotonic vehicle such as Sodium Chloride Injection, Ringer's Injection, Dextrose Injection, Dextrose and Sodium Chloride Injection, Lactated Ringer's Injection Citrate Buffer pH 5.5, or other vehicle as known in the art. The pharmaceutical composition of the present invention may also contain stabilizers, preservatives, buffers, antioxidants, or other additive known to those of skill in the art.

As noted above, the compositions can also include an appropriate carrier. For topical use, any of the conventional excipients may be added to formulate the active ingredients into a lotion, ointment, powder, cream, spray, or aerosol. For surgical implantation, the active ingredients may be combined with any of the well-known biodegradable and bioerodible carriers, such as polylactic acid and collagen formulations. Such materials may be in the form of solid implants, sutures, sponges, wound dressings, and the like. In any event, for local use of the materials, the active ingredients usually be present in the carrier or excipient in a weight ratio of from about 1:1000 to 1:20,000, but are not limited to ratios within this range. Preparation of compositions for local use are detailed in *Remington's Pharmaceutical Sciences*, latest edition, (Mack Publishing).

In a preferred therapeutic method, the peptide composition is provided in an IV infusion in the range of from 1 mg of active intredient/kg-4 mg/kg of body weight once a day.

As noted, preferred amounts and modes of administration are able to be determined by one skilled in the art. One skilled in the art of preparing formulations can readily select the proper form and mode of administration depending upon the particular characteristics of the compound selected, the infection to be treated, the stage of the infection, and other relevant circumstances using formulation technology known in the art, described, for example, in *Remington's Pharmaceutical Sciences*, latest edition, Mack Publishing Co.

Pharmaceutical compositions can be manufactured utilizing techniques known in the art. Typically the therapeutically effective amount of the peptide will be admixed with a pharmaceutically acceptable carrier.

The invention further includes a method of treating a topical fungal infection by topically applying an amount of the peptide sufficient to treat the infection, e.g., 0.5-10%. The topical medication may take any number of standard forms such as pastes, gels, creams, and ointments. Topical application may be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

The amount of peptide in the pharmaceutical composition of the present invention will depend upon the nature and severity of the condition being treated, and on the nature of prior treatments which the patient has undergone. Ultimately, the attending physician will decide the amount of peptide with which to treat each individual patient. Initially, the attending physician will preferably administer low doses of peptide and observe the patient's response. Larger doses of peptide may be administered until the optimal therapeutic effect is obtained for the patient, and at that point the dosage is not increased further. Without wishing to be held to a specific dosage, it is contemplated that the various pharmaceutical compositions used to practice the method of the present invention should contain about 0.1 mg to about 1000 mg of peptide per kg body weight per dose.

The duration of intravenous therapy using the pharmaceutical composition of the present invention will vary, depending on the severity of the disease being treated and the condition and potential idiosyncratic response of each individual patient. It is contemplated that the duration of each application of the peptide will be in the range of 1 to 2 hours and given once every 12 or 24 hours by continuous intravenous administration. Ultimately the attending physician will decide on the appropriate duration of intravenous therapy using the pharmaceutical composition of the present invention.

Other antibiotics, intravenous fluids, cardiovascular and respiratory support could also be provided if requested by the attending physician in a manner known to one of ordinary skill in the art.

Fungal diseases which may be treated by the peptide compositions described herein include but are not limited to: *Candida* spp., *Saccharomyces cerevisiae*, *Histoplasma capsulatum* and other *histoplasma* species which cause histoplasmosis, *Aspergillus fumigatus* and other species (occurring mostly in the lung), which causes Aspergillosis, and *Cryptococcus neoformans* (sometimes found in the lung but mostly in the central nervous system), which causes a disease known as cryptococcosis.

Additional pharmaceutical methods may be employed to control the duration of action of the peptide. Increased half-life and controlled release preparations may be achieved through the use of polymers to conjugate, complex with, or absorb the peptide described herein. The controlled delivery and/or increased half-life may be achieved by selecting appropriate macromolecules (for example, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide, and the appropriate concentration of macromolecules as well as the methods of incorporation, in order to control release.

Another possible method useful in controlling the duration of action by controlled release preparations and half-life is incorporation of the peptide molecule or its functional derivatives into particles of a polymeric material such as polyesters, polyamides, polyamino acids, hydrogels, poly(lactic acid), ethylene vinylacetate copolymers, copolymer micelles of, for example, PEG and poly(l-aspartamide).

The half-life of the peptides described herein can be extended by their being conjugated to other molecules such as polymers using methods known in the art to form drug-polymer conjugates. For example, the peptide can be bound (e.g., covalently) to molecules of inert polymers known in the art, such as a molecule of polyethylene glycol (PEG) in a method known as "pegylation". Pegylation can therefore extend the in vivo lifetime and thus therapeutic effectiveness of the peptide molecule. Pegylation also reduces the potential antigenicity of the peptide molecule. Pegylation can also enhance the solubility of the peptides thereby improving their therapeutic effect. PEGs used may be linear or branched-chain.

PEG molecules can be modified by functional groups, for example as shown in Harris et al., "Pegylation, A Novel Process for Modifying Phararmacokinetics", *Clin Pharmacokinet,* 2001:40(7); 539-551, and the amino group of the amino terminal residue of the peptide or an internal cysteine residue, or other amino acid having a linking group (eg. arginine, lysine, histidine, serine, threonine or methionine) therein can be linked thereto, wherein the PEG molecule can carry one or a plurality of one or more types of the peptides or, the peptide can carry more than one PEG molecule.

By "pegylated peptide" is meant a peptide of the present invention having a polyethylene glycol (PEG) moiety covalently bound to an amino acid residue or linking group of the peptide. The PEG molecule can also be attached to the peptide via a linker comprising one to ten amino acids for example.

By "polyethylene glycol" or "PEG" is meant a polyalkylene glycol compound or a derivative thereof, with or without coupling agents or derviatization with coupling or activating moeities (e.g., with thiol, triflate, tresylate, azirdine, oxirane, or preferably with a maleimide moiety). Compounds such as maleimido monomethoxy PEG are exemplary or activated PEG compounds of the invention. Other polyalkylene glycol compounds, such as polypropylene glycol, may be used in the present invention. Other appropriate polymer conjugates include, but are not limited to, non-polypeptide polymers, charged or neutral polymers of the following types: dextran, colominic acids or other carbohydrate based polymers, biotin deriviatives and dendrimers, for example. The term PEG is also meant to include other polymers of the class polyalkylene oxides.

The PEG can be linked to any N-terminal amino acid of the peptide, and/or can be linked to an amino acid residue downstream of the N-terminal amino acid, such as lysine, histidine, tryptophan, aspartic acid, glutamic acid, serine, threonine, methionine, and cysteine, for example or other such amino acids known to those of skill in the art. Cysteine-pegylated peptides, for example, are created by attaching polyethylene glycol to a SH group on a cysteine residue of the peptide.

The chemically modified peptides contain at least one PEG moiety, preferably at least two PEG moieties, up to a maximum number of PEG moieties bound to the peptide without abolishing activity, e.g., the PEG moiety(ies) are bound to an amino acid residue preferably at or near the N-terminal portion of the peptide.

The PEG moiety attached to the protein preferably ranges in molecular weight from about 200 to 30,000 MW. Preferably the PEG moiety will be from about 1,000 to 8,000 MW, more preferably from about 3,250 to 5,000 MW, most preferably about 5,000 MW.

The actual number of PEG molecules covalently bound per chemically modified peptide of the invention may vary widely depending upon the desired peptide stability (i.e. serum half-life).

Peptide molecules contemplated for use herein can be linked to PEG molecules using techniques shown, for example (but not limited to), in U.S. Pat. Nos. 4,179,337; 5,382,657; 5,972,885; 6,177,087; 6,165,509; 5,766,897; and 6,217,869; the specifications and drawings each of which are hereby expressly incorporated herein by reference in their entirety.

Alternatively, it is possible to entrap the peptides in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in the latest edition of *Remington's Pharmaceutical Sciences.*

U.S. Pat. No. 4,789,734 describe methods for encapsulating biochemicals in liposomes and is hereby expressly incorporated by reference herein. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine,* pp. 287-341 (Academic Press, 1979). Microspheres formed of polymers or proteins are well known to those skilled in the art, and can be tailored for passage through the gastrointestinal tract directly into the blood stream. Alternatively, the agents can be incorporated and the microspheres, or composite of microspheres, implanted for slow release over a period of time, ranging from days to months. See, for example, U.S. Pat. Nos. 4,906,474; 4,925,673; and 3,625,214 which are incorporated by reference herein.

When the composition is to be used as an injectable material, it can be formulated into a conventional injectable carrier. Suitable carriers include biocompatible and pharmaceutically acceptable phosphate buffered saline solutions, which are preferably isotonic.

For reconstitution of a lyophilized product in accordance with this invention, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field.

The pharmaceutical composition may also be in the form of an aqueous solution containing many of the same substances as described above for the reconstitution of a lyophilized product.

The compounds can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the compounds of the invention may be incorporated into pharmaceutical preparations which may be used for therapeutic purposes. However, the term "pharmaceutical preparation" is intended in a broader sense herein to include preparations containing a peptide composition in accordance with this invention, used not only for therapeutic purposes but also for reagent or diagnostic purposes as known in the art, or for tissue culture. The pharmaceutical preparation intended for therapeutic use should contain a "pharmaceutically acceptable" or "therapeutically effective amount" of a peptide, i.e., that amount necessary for preventative or curative health measures. If the pharmaceutical preparation is to be employed as a reagent or diagnostic, then it should contain reagent or diagnostic amounts of a peptide.

All of the assay methods listed herein are well within the ability of one of ordinary skill in the art given the teachings provided herein.

While the invention is described herein in connection with certain embodiments so that aspects thereof may be more fully understood and appreciated, it is not intended that the invention be limited to these particular embodiments. On the contrary, it is intended that all alternatives, modifications and equivalents are included within the scope of the invention as defined herein. Thus the examples described above, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention. Changes may be made in the formulation of the various compositions described herein or in the steps or the sequence of steps of the methods described herein without departing from the spirit and scope of the invention as described herein.

All references, articles, and patent applications cited herein are hereby expressly incorporated herein in their entirety by reference.

CITED REFERENCES

Brackett, D. J., M. R. Lerner, M. A. Lacquement, R. He, and H. A. Pereira. 1997. A synthetic lipopolysaccharide-binding peptide based on the neutrophil-derived protein CAP37 prevents endotoxin-induced responses in conscious rats. Infect. Immun. 65:2803-2811.

Clark, T. A. and R. A. Hajjeh. 2002. Recent trends in the epidemiology of invasive mycoses. Curr. Opin. Infect. Dis. 15:569-574.

Dale, B. A. 2000. Periodontal epithelium: a newly recognized role in health and disease. Periodontal. 30:70-78.

Dale, B. A., and S. Krisanaprakornkit. 2001. Defensin antimicrobial peptides in the oral cavity. J. Oral Pathol. Med. 30:321-327.

Diamond, G., D. Legarda, and L. K. Ryan. 2000. The innate immune response of the respiratory epithelium. Immunol Rev. 173:27-38.

Edgerton M, S. E. Koshlukova, M. W. B. Araujo, R. C. Patel, J. Dong, and J. A. Bruenn. 2000. Salivary histatin 5 and human neutrophil defensins 1 kill *Candida albicans* via shared pathways. Antimicrob. Agents Chemother. 44:3310-3316.

Fellermann, K. and E. F. Stange. 2001. Defensins—innate immunity at the epithelial frontier. Eur. J. Gastroenterol. Hepatol. 13:771-778.

Frohm-Nilsson, F., B. Sandstedt, O. Sørensen, G. Weber, N. Borregaard, and M. Ståhle-Bäckdahl. 1999. The human cationic antimicrobial protein (hCAP18), a peptide antibiotic, is widely expressed in human squamous epithelia and colocalizes with interleukin-6. Infect. Immun. 67:2561-2566.

Ganz, T. and J. Weiss. 1997. Antimicrobial peptides of phagocytes and epithelial. Semin. Hematol. 34:343-354.

Gonzalez M. L., X. Ruan, P. Kumar, P. Grammas, and H. A. Pereira. 2004. Functional modulation of smooth muscle cells by the inflammatory mediator CAP37. Microvasc. Res. 67:168-181.

Hancock, R. E. W. 1997. Peptide antibiotics. Lancet 349:418-422.

Helmerhorst E. J., W. Van 'T Hof, E. C. I. Veerman, I. Simoons-Smit and A. V. Nieuw Amerongen. 1997. Synthetic histatin analogues with broad spectrum antimicrobial activity. Biochem. J. 326:39-45.

Helmerhorst, E. J., I. M. Reijnders, W. Van 'T Hof, I. Simoons-Smit, E. C. I. Veerman, and A. V. Nieuw Amerongen. 1999. Amphotericin B- and Fluconazole-resistant *Candida* spp., *Aspergillus fumigatus*, and other newly emerging pathogenic fungi are susceptible to basic antifungal peptides. Antimicrob. Agents Chemother. 43:702-704.

Hiemstra, P.S. 2001. Epithelial antimicrobial peptides and proteins: their role in host defense and inflammation. Pediatr. Respir. Rev. 2:306-310.

Hobson R. P. 2003. The global epidemiology of invasive *Candida* infections—is the tide turning? J. Hosp. Infect. 55:159-168.

Hoover, D. M., Z. Wu, K. Tucker, Y. Lu, and J. Lubkowski. 2003. Antimicrobial characterization of human β-defensin 3 derivatives. Antimicrob. Agents Chemother. 47:2804-2809.

Huttner, K. M., and C. L. Bevins. 1999. Antimicrobial peptides as mediators of epithelial host defense. Pediatr. Res. 45:785-794.

Jabra-Rizk, M. A., W. A. Falkler, and T. F. Meiller. 2004. Fungal biofilms and drug resistance. Emerging Infect. Dis. 10:14-19.

J. Davies, J. Peptide Sci. 9:471-507(2003).

Kuhn, D. M., P. K. Mukherjee, T. A. Clark, C. Pujol, J. Chandra, R. A. Hajjeh, D. W. Warnock, D. R. Soll, and M. A. Ghannoum. 2004. *Candida parapsilosis*. Characterization in an outbreak setting. Emerging Infect. Dis. 6:1074-1081.

Lee, T. D., M. L. Gonzalez, P. Kumar, P. Grammas and H. A. Pereira. 2003. CAP37, a neutrophil-derived inflammatory mediator augments leukocyte adhesion to endothelial monolayers. Microvasc. Res. 66:38-48.

Lee, T. D., M. L. Gonzalez, P. Kumar, S. Chary-Reddy, P. Grammas, and H.A. Pereira. 2002. CAP37, a novel inflammatory mediator. Its expression in endothelial cells and localization to atherosclerotic plaques. Am. J. Pathol. 160:841-848.

Lupetti, A., Paulusma-Annema, M. M. Welling, S. Senesi, J. T. Van Dissel, and P. H. Nibbering. 2000. Candidacidal activities of human lactoferrin peptides derived from the N terminus. Antimicrob. Agents Chemother. 44:3257-3263.

Malm, J., O. Sørensen, T. Persson, M. Frohm-Nilsson, B. Johansson, A. Bjartell, H. Lilja, M. Ståhle-Bäckdahl, N. Borregaard, and A. Egesten. 2000. The human cationic antimicrobial protein (hCAP-18) is expressed in the epithelium of human epididymis, is present in seminal plasma at high concentrations and is attached to spermatozoa. Infect. Immun. 68:4297-4302.

M. Hornef, et al. Nat. Immunol. 5(8):836-843(2004).

Nizet, V., T. Ohtake, X. Lauth, J. Trowbridge, J. Rudisill, R. A. Dorchner, V. Pestonjamasp, J. Piraino, K. Huttner, and R.

L. Gallo. 2001. Innate antimicrobial peptide protects the skin from invasive bacterial infection. Nature 414:454-457.

Nola I, K. Kostovic, L. Oremovic, A. Soldo-Belic, and L. Lugovic. 2003. *Candida* infections today—how big is the problem? Acta Dermatovenerol Croat. 11:171-177.

Oren, A., T. Ganz, L. Liu, and Meerloo T. 2003. In human epidermis, beta defensin 2 is packaged in lamellar bodies. Exp. Mol. Pathol. 74:180-182.

Pereira, H. A., W. M. Shafer, J. Pohl, L. E. Martin, and J. K. Spitznagel. 1990. CAP37, a human neutrophil-derived chemotactic factor with monocyte specific activity. J. Clin Invest. 85:1468-1476.

Pereira, H. A., I. Erdem, J. Pohl, and J. K. Spitznagel. 1993. Synthetic bactericidal peptide based on CAP37: a 37 kDa human neutrophil granule-associated cationic antimicrobial protein chemotactic for monocytes. Proc. Natl. Acad. Sci. (USA). 90:4733-4737.

Pereira, H. A., P. Kumar, and P. Grammas. 1996. Expression of CAP37, a novel inflammatory mediator in Alzheimer's disease. Neurobiol. Aging 17:753-759.

Pereira, H. A., X. Ruan, and P. Kumar. 2003. Activation of microglia: a neuroinflammatory role for CAP37. GLIA 41:64-72.

Pereira, H. A., P. Kumar, M. R. Lerner, and D. J. Brackett. (2004) Inducible expression of the inflammatory protein CAP37 in the epidermis during wound healing, p. 127-144. In J. W. Robinson (ed.), Focus on Protein Research. Nova Biomedical Publications, Hauppauge, N.Y.

P. Li and P. Roller. Can. Top. In Med. Chem. 2:325-341 (2002).

Pohl, J., H. A. Pereira, N. M. Martin, and J. K. Spitznagel. 1990. Amino acid sequence of CAP37, a human neutrophil granule-derived antibacterial and monocyte-specific chemotactic glycoprotein structurally similar to neutrophil elastase. FEBS Lett. 272:200-204.

Rapp R. P. 2004. Changing strategies for the management of invasive fungal infections. Pharmacotherapy 24:4S-28S.

Ruan, X., J. Chodosh, M. C. Callegan, M. C. Booth, T. D. Lee, P. Kumar, Gilmore, M. S., and H. A. Pereira. 2002. Corneal expression of the inflammatory mediator CAP37. Invest. Ophthalmol. Vis. Sci. 43:1414-1421.

Selsted, M. E., D. Szklarek, T. Ganz, and R. I. Lehrer. 1985. Activity of rabbit leukocyte peptides against *Candida albicans*. Infect. Immun. 49:202-206.

Shafer, W. M., L. E. Martin, and J. K. Spitznagel. 1984. Cationic antimicrobial proteins isolated from human neutrophil granulocytes in the presence of diisopropyl fluorophosphate. Infect. Immun. 45:29-35.

Shafer, W. M., L. E. Martin, and J. K. Spitznagel. 1986. Late intraphagosomal hydrogen ion concentration favors the in vitro antimicrobial capacity of a 37-kilodalton cationic granule protein of human neutrophil granules. Infect. Immun. 53:651-655.

Shirafuji Y, T. Oono, H. Kanzaki, S. Hirakawa, and J. Arata. 1999. Detection of cryptdin in mouse skin. Clin. Diagn. Lab. Immunol. 6:336-340.

Sørensen O. E., J. B. Cowland, K. Theilgaard-Mönch, L. Liu, T. Ganz, and N. Borregaard. 2003. Wound healing and expression of antimicrobial peptides/polypeptides in human keratinocytes, a consequence of common growth factors. J. Immunol. 170:5583-5589.

Situ, H., H. Tsai, and L. A. Bobek. 1999. Construction and characterization of human salivary histtin-5 multimers. J. Dent. Res. 78:690-698.

Spitznagel, J. K. 1990. Antibiotic proteins of human neutrophils. J. Clin. Invest. 86:1381-1386.

Sullivan, D. J., G. P. Morgan, E. Pinjon, A. Al-Mosaid, C. Stokes, C. Vaughan, and D.C. Coleman. 2004. Comparison of the epidemiology, drug resistance mechanisms, and virulence of *Candida dubliniensis* and *Candida albicans*. FEMS Yeast Res. 4:369-376.

Tang, Y-Q, M. R. Yeaman, and M. E. Selsted. 2002. Antimicrobial peptides from human platelets. Infect. Immun. 70:6524-6533.

Technical Report TI-PEP05-0405 of Thermo Electron Corp. 2005.

Tsai, H., P. A. Raj, and L. A. Bobek. 1996. Candidacidal activity of recombinant human salivary histatin-5 and variants. Infect. Immun. 64:5000-5007.

Tsai H. and L. A. Bobek. 1997. Studies of the mechanism of human salivary histatin-5 candidacidal activity with histatin-5 variants and azole-sensitive and -resistant *Candida* species. Antimicrob. Agents Chemother. 41:2224-2228.

Warn, P. A., A. Sharp, G. Morrissey, and D. W. Denning. 2002. In vivo activity of micafungin in a persistently neutropenic murine model of disseminated infection caused by *Candida tropicalis*. J. Antimicrob. Chemother. 50:1071-1074.

What is claimed is:

1. A method of treating a fungal infection in a subject in need of such treatment, comprising:
   administering to the subject in need of treatment of the fungal infection a therapeutically effective amount of a peptide having 20-25 amino acids, the peptide comprising SEQ ID NO:5, SEQ ID NO:6, SEQ ID NO:7, SEQ ID NO:8, SEQ ID NO:12, SEQ ID NO:13, or SEQ ID NO:14, and wherein the peptide comprises an arginine residue immediately adjacent to a histidine residue.

2. The method of claim 1 wherein the peptide comprises SEQ ID NO: 6 or SEQ ID NO: 12.

3. The method of claim 1 wherein the peptide comprises SEQ ID NO: 7 or SEQ ID NO: 13.

4. The method of claim 1 wherein the peptide comprises SEQ ID NO: 8 or SEQ ID NO: 14.

5. The method of claim 1 wherein the fungal infection treated in the subject is caused by at least one of a *Candida* spp., *Saccharomyces cerevisiae*, *Histoplasma* spp., *Aspergillus* spp., and *Cryptococcus* spp.

6. The method of claim 1 wherein the subject is a mammal.

7. The method of claim 1 wherein the subject is a human.

8. The method of claim 1 wherein the peptide has from one to three additional amino acids on an N-terminal end of the peptide and one to two additional amino acids on a C-terminal end of the peptide.

9. The method of claim 1 wherein the peptide is pegylated.

10. The method of claim 1 wherein the peptide is covalently pegylated to a polyethylene glycol molecule via a linker molecule comprising 1 to 15 amino acids.

11. A method of treating a fungal infection in a subject in need of such treatment, comprising:
   administering to the subject in need of treatment of the fungal infection a therapeutically effective amount of a peptide comprising 20 to 25 amino acids, the peptide comprising the sequence (SEQ ID NO: 15):

$R$-$H$-$X_3$-$X_4$-$X_5$-$X_6$-$X_7$-$X_8$-$X_9$-$H$-$X_{11}$-$R$-$X_{13}$-$X_{14}$-$M$-$X_{16}$-$X_{17}$-$X_{18}$-$X_{19}$-$X_{20}$ wherein:
   $X_3$ is phe, tyr, arg, lys or his;
   $X_4$ is cys, ser, thr, arg, lys or his;
   $X_5$ is gly, ala, arg, lys or his;
   $X_6$ is gly, ala, arg, lys or his;
   $X_8$, $X_9$, $X_{17}$, and $X_{18}$ are selected from the group consisting of ala, leu, ile and val;
   $X_7$, $X_{11}$ and $X_{14}$ are selected from the group consisting of ala, leu, ile, val, arg, lys, and his;
   $X_{13}$ is phe or tyr;
   $X_{16}$ is ser or thr;
   $X_{19}$ is ser, thr, his, arg or lys;
   $X_{20}$ is ser, cys or thr;
   R is arg;
   H is his; and
   M is met.

12. The method of claim 1 wherein the $X_4$ is cys and the $X_{20}$ is serine or threonine.

13. The method of claim 1 wherein the $X_{20}$ is cys and the $X_4$ is serine or threonine.

14. The method of claim 1 wherein in the peptide:
   $X_3$ and $X_{13}$ are selected from the group consisting of phe and tyr;
   $X_4$ and $X_{20}$ are selected from the group consisting of cys, ser, and thr;
   $X_5$ and $X_6$ are selected from the group consisting of gly and ala;
   $X_7$, $X_8$, $X_9$, $X_{11}$, $X_{14}$, $X_{17}$ and $X_{18}$ are selected from the group consisting of ala, leu, ile, and val;
   $X_{16}$ is ser or thr; and
   $X_{19}$ is ser, thr, his, arg, or lys.

15. The method of claim 1 wherein the fungal infection treated in the subject is caused by at least one of a *Candida* spp., *Saccharomyces cerevisiae*, *Histoplasma* spp., *Aspergillus* spp., and *Cryptococcus* spp.

16. The method of claim 1 wherein the subject is a mammal.

17. The method of claim 1 wherein the subject is human.

18. The method of claim 1 wherein the peptide has from one to three additional amino acids on an N-terminal end of the peptide and one to two additional amino acids on a C-terminal end of the peptide.

19. The method of claim 1 wherein the peptide is pegylated.

20. The method of claim 1 wherein the peptide is covalently pegylated to a polyethylene glycol molecule via a linker molecule comprising 1 to 15 amino acids.

* * * * *

UNITED STATES PATENT AND TRADEMARK OFFICE
CERTIFICATE OF CORRECTION

PATENT NO. : 7,745,401 B2
APPLICATION NO. : 11/497178
DATED : June 29, 2010
INVENTOR(S) : H. Anne Pereira and Paul Fidel It is certified that error appears in the above-identified patent and that said Letters Patent is hereby corrected as shown below:

Column 2, line 4: After "BRIEF DESCRIPTION OF THE DRAWINGS" insert the following paragraph,
-- This patent or application file contains at least one drawing executed in color. Copies of this patent or patent application publication with color drawing(s) will be provided by the Office upon request and payment of the necessary fee. --

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,745,401 B2
APPLICATION NO. : 11/497178
DATED : June 29, 2010
INVENTOR(S) : Pereira et al.

Page 1 of 1

It is certified that error appears in the above-identified patent and that said Letters Patent is hereby corrected as shown below:

In the Specification

Column 1, Lines 15-18: Delete entirety of paragraph and replace with -- This invention was made with government support under Grant AI028018 awarded by the National Institutes of Health. The government has certain rights in the invention. --

Signed and Sealed this
Fourteenth Day of December, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 16

<210> SEQ ID NO 1
<211> LENGTH: 25
<212> TYPE: PRT
<213> ORGANISM: Homo sapiens

<400> SEQUENCE: 1

Asn Gln Gly Arg His Phe Cys Gly Gly Ala Leu Ile His Ala Arg Phe
1               5                   10                  15

Val Met Thr Ala Ala Ser Cys Phe Gln
            20                  25

<210> SEQ ID NO 2
<211> LENGTH: 25
<212> TYPE: PRT
```

```
<213> ORGANISM: Homo sapiens

<400> SEQUENCE: 2

Asn Gln Gly Arg His Phe Ser Gly Gly Ala Leu Ile His Ala Arg Phe
1               5                   10                  15

Val Met Thr Ala Ala Ser Cys Phe Gln
            20                  25

<210> SEQ ID NO 3
<211> LENGTH: 25
<212> TYPE: PRT
<213> ORGANISM: Homo sapiens

<400> SEQUENCE: 3

Asn Gln Gly Arg His Phe Cys Gly Gly Ala Leu Ile His Ala Arg Phe
1               5                   10                  15

Val Met Thr Ala Ala Ser Ser Phe Gln
            20                  25

<210> SEQ ID NO 4
<211> LENGTH: 25
<212> TYPE: PRT
<213> ORGANISM: Homo sapiens

<400> SEQUENCE: 4

Asn Gln Gly Arg His Phe Ser Gly Gly Ala Leu Ile His Ala Arg Phe
1               5                   10                  15

Val Met Thr Ala Ala Ser Ser Phe Gln
            20                  25

<210> SEQ ID NO 5
<211> LENGTH: 20
<212> TYPE: PRT
<213> ORGANISM: Homo sapiens

<400> SEQUENCE: 5

Arg His Phe Cys Gly Gly Ala Leu Ile His Ala Arg Phe Val Met Thr
1               5                   10                  15

Ala Ala Ser Cys
            20

<210> SEQ ID NO 6
<211> LENGTH: 20
<212> TYPE: PRT
<213> ORGANISM: Homo sapiens

<400> SEQUENCE: 6

Arg His Phe Ser Gly Gly Ala Leu Ile His Ala Arg Phe Val Met Thr
1               5                   10                  15

Ala Ala Ser Cys
            20

<210> SEQ ID NO 7
<211> LENGTH: 20
<212> TYPE: PRT
<213> ORGANISM: Homo sapiens

<400> SEQUENCE: 7

Arg His Phe Cys Gly Gly Ala Leu Ile His Ala Arg Phe Val Met Thr
1               5                   10                  15

Ala Ala Ser Ser
            20
```

<210> SEQ ID NO 8
<211> LENGTH: 20
<212> TYPE: PRT
<213> ORGANISM: Homo sapiens

<400> SEQUENCE: 8

Arg His Phe Ser Gly Gly Ala Leu Ile His Ala Arg Phe Val Met Thr
1               5                   10                  15

Ala Ala Ser Ser
            20

<210> SEQ ID NO 9
<211> LENGTH: 25
<212> TYPE: PRT
<213> ORGANISM: Homo sapiens

<400> SEQUENCE: 9

Asn Gln Gly Arg His Phe Thr Gly Gly Ala Leu Ile His Ala Arg Phe
1               5                   10                  15

Val Met Thr Ala Ala Ser Cys Phe Gln
            20                  25

<210> SEQ ID NO 10
<211> LENGTH: 25
<212> TYPE: PRT
<213> ORGANISM: Homo sapiens

<400> SEQUENCE: 10

Asn Gln Gly Arg His Phe Cys Gly Gly Ala Leu Ile His Ala Arg Phe
1               5                   10                  15

Val Met Thr Ala Ala Ser Thr Phe Gln
            20                  25

<210> SEQ ID NO 11
<211> LENGTH: 25
<212> TYPE: PRT
<213> ORGANISM: Homo sapiens

<400> SEQUENCE: 11

Asn Gln Gly Arg His Phe Thr Gly Gly Ala Leu Ile His Ala Arg Phe
1               5                   10                  15

Val Met Thr Ala Ala Ser Thr Phe Gln
            20                  25

<210> SEQ ID NO 12
<211> LENGTH: 20
<212> TYPE: PRT
<213> ORGANISM: Homo sapiens

<400> SEQUENCE: 12

Arg His Phe Thr Gly Gly Ala Leu Ile His Ala Arg Phe Val Met Thr
1               5                   10                  15

Ala Ala Ser Cys
            20

<210> SEQ ID NO 13
<211> LENGTH: 20
<212> TYPE: PRT
<213> ORGANISM: Homo sapiens

<400> SEQUENCE: 13

```
Arg His Phe Cys Gly Gly Ala Leu Ile His Ala Arg Phe Val Met Thr
1               5                   10                  15

Ala Ala Ser Thr
            20

<210> SEQ ID NO 14
<211> LENGTH: 20
<212> TYPE: PRT
<213> ORGANISM: Homo sapiens

<400> SEQUENCE: 14

Arg His Phe Thr Gly Gly Ala Leu Ile His Ala Arg Phe Val Met Thr
1               5                   10                  15

Ala Ala Ser Thr
            20

<210> SEQ ID NO 15
<211> LENGTH: 20
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: phe, tyr, arg, lys, or his
<220> FEATURE:
<221> NAME/KEY: MISC_FEATURE
<222> LOCATION: (4)..(4)
<223> OTHER INFORMATION: cys, ser, thr, arg, lys, or his
<220> FEATURE:
<221> NAME/KEY: MISC_FEATURE
<222> LOCATION: (5)..(5)
<223> OTHER INFORMATION: gly, ala, arg, lys, or his
<220> FEATURE:
<221> NAME/KEY: MISC_FEATURE
<222> LOCATION: (6)..(6)
<223> OTHER INFORMATION: gly, ala, arg, lys, or his
<220> FEATURE:
<221> NAME/KEY: MISC_FEATURE
<222> LOCATION: (7)..(7)
<223> OTHER INFORMATION: ala, leu, ile, val, arg, lys, or his
<220> FEATURE:
<221> NAME/KEY: MISC_FEATURE
<222> LOCATION: (8)..(8)
<223> OTHER INFORMATION: ala, leu, ile, or val
<220> FEATURE:
<221> NAME/KEY: MISC_FEATURE
<222> LOCATION: (9)..(9)
<223> OTHER INFORMATION: ala, leu, ile, or val
<220> FEATURE:
<221> NAME/KEY: MISC_FEATURE
<222> LOCATION: (11)..(11)
<223> OTHER INFORMATION: ala, leu, ile, val, arg, lys, or his
<220> FEATURE:
<221> NAME/KEY: MISC_FEATURE
<222> LOCATION: (13)..(13)
<223> OTHER INFORMATION: phe or tyr
<220> FEATURE:
<221> NAME/KEY: MISC_FEATURE
<222> LOCATION: (14)..(14)
<223> OTHER INFORMATION: ala, leu, ile, val, arg, lys, or his
<220> FEATURE:
<221> NAME/KEY: MISC_FEATURE
<222> LOCATION: (16)..(16)
<223> OTHER INFORMATION: ser or thr
<220> FEATURE:
<221> NAME/KEY: MISC_FEATURE
<222> LOCATION: (17)..(17)
<223> OTHER INFORMATION: ala, leu, ile, or val
<220> FEATURE:
<221> NAME/KEY: MISC_FEATURE
<222> LOCATION: (18)..(18)
<223> OTHER INFORMATION: ala, leu, ile, or val
```

```
<220> FEATURE:
<221> NAME/KEY: MISC_FEATURE
<222> LOCATION: (19)..(19)
<223> OTHER INFORMATION: ser, thr, his, arg, or lys
<220> FEATURE:
<221> NAME/KEY: MISC_FEATURE
<222> LOCATION: (20)..(20)
<223> OTHER INFORMATION: cys, ser, or thr

<400> SEQUENCE: 15

Arg His Xaa Xaa Xaa Xaa Xaa Xaa Xaa His Xaa Arg Xaa Xaa Met Xaa
1               5                   10                  15

Xaa Xaa Xaa Xaa
            20

<210> SEQ ID NO 16
<211> LENGTH: 27
<212> TYPE: PRT
<213> ORGANISM: Homo sapiens

<400> SEQUENCE: 16

Gly Thr Arg Cys Gln Val Ala Gly Trp Gly Ser Gln Arg Ser Gly Gly
1               5                   10                  15

Arg Leu Ser Arg Phe Pro Arg Phe Val Asn Val
            20                  25
```